United States Patent [19]

Shen

[11] Patent Number: 5,777,178

[45] Date of Patent: Jul. 7, 1998

[54] PROCESS FOR THE PREPARATION OF POLYOXYALKYLENE ETHER SURFACTANT COMPOSITIONS

[75] Inventor: Ming Shen, Guilford, Conn.

[73] Assignee: Olin Corporation, Cheshire, Conn.

[21] Appl. No.: 769,619

[22] Filed: Dec. 18, 1996

[51] Int. Cl.⁶ ..................................... C07C 41/03
[52] U.S. Cl. ................ 568/679; 568/618; 514/723
[58] Field of Search .................... 568/679, 618; 514/723

[56] References Cited

U.S. PATENT DOCUMENTS

| | | | |
|---|---|---|---|
| 2,979,533 | 4/1961 | Bruson et al. | 260/613 |
| 3,711,412 | 1/1973 | Sawyer et al. | 252/73 |
| 3,887,624 | 6/1975 | Gipson et al. | 260/615 B |
| 3,997,613 | 12/1976 | Lenke et al. | 260/481 R |
| 4,408,084 | 10/1983 | Langdon | 568/601 |
| 4,418,217 | 11/1983 | Schmid et al. | 568/593 |
| 4,491,676 | 1/1985 | Eagar et al. | 568/449 |
| 4,519,950 | 5/1985 | Langdon | 260/404 |
| 5,254,744 | 10/1993 | Neumer | 568/601 |
| 5,378,485 | 1/1995 | Mahler et al. | 426/329 |
| 5,492,631 | 2/1996 | Koester et al. | 210/729 |

FOREIGN PATENT DOCUMENTS

| | | | |
|---|---|---|---|
| 25 23 588 | 5/1975 | Germany | C08G 4/00 |
| 33 18592 A1 | 5/1983 | Germany | C07C 43/11 |

*Primary Examiner*—Gary Geist
*Assistant Examiner*—S. Padmanabhan
*Attorney, Agent, or Firm*—Todd E. Garabedian; Wiggin & Dana

[57] ABSTRACT

The present invention is directed to a process for the preparation of polyoxyalkylene ether surfactant compositions comprising the steps of combining an admixture of alkoxylated alcohols with an acid catalyst and 1–6 molar equivalents of an aldehyde. The mixture is reacted at between about 50° C. and about 180° C. and at between about 1 atm and 10 atm pressure in the absence of a distillation step to produce the polyoxyalkylene ether surfactant composition.

12 Claims, No Drawings

PROCESS FOR THE PREPARATION OF POLYOXYALKYLENE ETHER SURFACTANT COMPOSITIONS

BACKGROUND OF THE INVENTION

1. Field of the Invention

The present invention relates to polyoxyalkylene ether surfactant compositions, and more particularly to a process of preparing polyoxyalkylene ether surfactant compositions that does not require removal of water by-product during the reaction.

2. Description of the Related Art

Polyoxyalkylene ethers prepared from the reaction of an alkoxylated alcohol with an aldehyde, or mixed alkoxylated alcohols with mixed aldehydes, have been reported in U.S. Pat. No. 2,979,533 and German disclosures DE 2523588 and DE 3318592. The polyoxyalkylene ethers prepared by these processes are useful as surfactants for a wide range of applications such as detergents, emulsifiers, wetting agents, penetrants, dyeing assistants, and the like. The processes described therein utilize continuous removal of the water by-product by azeotropic distillation with either a reaction solvent or a co-product formed under the same reaction conditions. Although simple evaporation of water without solvent might be a useful method to remove water as mentioned in the above U.S. patent, it is difficult to practice the process using aldehydes with boiling points lower than or about the same as water since the separation of these components from water is difficult.

Several other U.S. patents describe various processes for the production of polymers in which water is generated as a by-product. U.S. Pat. Nos. 4,408,084 and 4,519,950 to Langdon disclose preparation of surface-active agents made from low molecular weight polyoxyalkylene co-polymers, an aldehyde coupling agent, and a solvent. During reaction, solvent and water by-product is removed by azeotropic distillation.

U.S. Pat. No. 3,997,613 to Lenke et al. discloses a plasticizer made by reacting poly and mono alcohols with a carbonyl compound. Water generated during the reaction is removed by stripping in order to shift the reaction equilibrium to favor products.

U.S. Pat. No. 5,254,744 to Neumer discloses coupling poly(tetramethylene ether) glycols with formaldehyde. Water entrained in the solvent is continuously separated and collected in a Dean Stark trap by azeotropic distillation during the reaction.

U.S. Pat. No. 4,418,217 to Schmid et al. discloses a process for production of a mixed formal of polyglycol ethers. Water by-product is removed using azeotropic distillation during the reaction.

All of the above-mentioned prior art processes entail removal of water by distillation as it is formed during the reactions. However, the distillation step is disadvantageous for polymer production. Distillation is time consuming, energy intensive, and a solvent is required. In addition, the product yield can suffer if the boiling points of the reaction product and the solvent (e.g., water or an organic solvent) are not sufficiently different. Thus, there is a need in the art for a process of producing polyoxyalkylene ether surfactant compositions that does not employ removal of water by-product during the reaction. The present invention is believed to be an answer to that need.

SUMMARY OF THE INVENTION

In one aspect, the present invention is directed to a process for the preparation of polyoxyalkylene ether surfactant compositions having the formula

comprising the steps of providing an admixture of alkoxylated alcohols selected from the group consisting of $R_1$—O—$(XO)_1$—$(YO)_m$H and H$(OU)_p$—$(OV)_o$—$OR_2$ wherein $R_1$ and $R_2$ are independently selected from the group consisting of an alkyl or alkenyl groups having from 3 to 22 carbon atoms or a mono, di or trialkyl phenyl radical having from 14 to 26 carbon atoms, 1, m, p, o are each integers from 0 to 30, and l+m and o+p are at least 3, and X, Y, U, V are alkyl radicals. The admixture of alkoxylated alcohols is combined with an acid catalyst and aldehyde of the formula $R_3$—C(O)H wherein $R_3$ is H, an alkyl group, an alkenyl group, or an aryl group. The aldehyde is present in about 1–6 molar equivalents over the total moles of alkoxylated alcohols. The mixture is reacted at between about 50° C. and about 180° C. and at between about 1 atm and 10 atm pressure in the absence of a distillation step to produce the polyoxyalkylene ether surfactant composition. These and other aspects will become apparent upon reading the following detailed description of the invention.

DETAILED DESCRIPTION OF THE PREFERRED EMBODIMENTS OF THE INVENTION

The present invention is directed to a new method for the preparation of polyoxyalkylene ether surfactant compositions of formula (I):

where $R_1$ and $R_2$ are independently selected from the group consisting of $R_1$—O—$(XO)_1$—$(YO)_m$H and H$(OU)_p$—$(OV)_o$—$OR_2$ wherein $R_1$ and $R_2$ are independently selected from the group consisting of an alkyl or alkenyl groups having from 3 to 22 carbon atoms or a mono, di or trialkyl phenyl radical having from 14 to 26 carbon atoms. 1, m, p, and o are integers from 0 to about 30 and l+m and o+p are at least 3. X, Y, U, V are alkyl radicals, and $R_3$ is H, an alkyl group, an alkenyl group, or an aryl group.

Polyoxyalkylene ethers may be generated by condensation of an aldehyde with alkoxylated alcohols of various carbon chain lengths. In the presence of an acid catalyst, the condensation reaction produces polyoxyalkylene ethers and water as a by-product. Previous attempts at increasing the yield and purity of polyoxyalkylene ethers have been directed towards removing water by-product from the reaction mixture using various forms of distillation during the reaction process. This approach has the effect of shifting the equilibrium of the condensation reaction to favor the reaction products. However, distillation techniques are not practically useful in all situations, particularly when the boiling point of the desired polyoxyalkylene ether is close to that of water or an azeotrope of water. Distillation is also expensive since it is energy intensive and requires that additional separation equipment be employed in conjunction with the reaction vessel.

The process of the present invention allows for preparation of polyoxyalkylene ethers in the absence of a distillation step. The advantages of this method of preparing polyoxyalkylene ether surfactant compositions include lower energy costs, increased efficiency, and lower equipment costs. In addition, a solvent is not required to be present, and thus problems of dilution and solvent removal, i.e., by azeotropic distillation, are alleviated.

The reactants utilized in the method of the invention include alkoxylated alcohols of various carbon chain lengths and compositions. Preferably, the alkoxylated alcohols are of the formulas (II) and (III):

$$R_1-O(XO)_l(YO)_m-H \quad \text{(II)}$$

$$H(OU)_p(OV)_oO-R_2 \quad \text{(III)}$$

where $R_1$ and $R_2$ are independently selected from alkyl or alkenyl groups having from 3–22 carbon atoms, and preferably 6–18 carbon atoms. Alternatively, $R_1$ or $R_2$ may be a mono, di, or trialkyl phenyl radical having from 14–26 carbon atoms, and preferably 16–24 carbon atoms. l, m, n, and o are integers independently selected from 0–30, and l+m and o+p are each at least 3. X, Y, O, and V are alkyl units of from 2 to 5 carbon atoms; thus the ether chains $(XO)_l$, $(YO)_m$, $(OU)_o$, and $(OV)_p$ are alkoxy units such as ethoxy, propoxy, isopropoxy, butoxy, pentoxy, and the like.

The alkoxylated alcohols used as reactants in the process of the present invention may be prepared by conventional methods known in the art, such as reaction of an alcohol compound with an alkyl oxide or a mixture of alkyl oxides. Such a reaction produces an alkoxylated alcohol of desired composition for reaction into the desired polyoxyalkylene ethers. For example, an alkanol, such as a straight-chain alkanol, may be reacted with a mixture of alkyl oxides, such as propylene oxide and ethylene oxide. The propylene oxide and ethylene oxide may be present in the same molar ratio or in different molar ratios to produce long-chain alkoxylated alcohols that include various alkoxy units. This flexibility permits the user to generate polyoxyalkylene ethers of any desired composition.

Aldehydes useful in the process of the present invention include, but are not limited to, formaldehyde, acetaldehyde, propionaldehyde, butyraldehyde, benzaldehyde, and combinations thereof. Aldehydes of higher carbon numbers may also be used. Alternatively, compounds which release formaldehyde during the reaction may also be used. Such aldehyde derivatives include trioxan, paraformaldehyde, and combinations thereof. The preferable use level of the aldehyde is from 1 to 6 molar equivalents over the total moles of alkoxylated alcohols, and more preferably from 1.5 to 3 molar equivalents over the total moles of alkoxylated alcohols.

An acid catalyst is added to the reaction mixture during the process of the invention. Useful acid catalysts include, but are not limited to, sulfuric acid, hydrochloric acid, phosphoric acid, organic sulfonic acids (i.e., p-tolunesulfonic acid), Lewis acids (i.e., zinc chloride), or strongly acidic ion-exchange resins. Alternatively, natural acid clays consisting of aluminum magnesium hydrosilicates may also be utilized. These clays are commercially available under the tradenames of "TONSIL" or "ATAPULGAS".

High concentrations of reactants are used in the process of the invention. Generally, each mole of alkoxylated alcohols are combined with about a 1 to 6 molar excess (with respect to total moles of alkoxylated alcohols) of aldehyde. The reactants are placed under pressure and high temperature during the reaction. The process of the present invention preferably takes place in an enclosed vessel such as a pressure reactor at a specified temperature and for a specified time. The reaction temperature is preferably between about 50° C. and 180° C., and more preferably between about 80° C. and 150° C. The reaction pressure is preferably about between 1 and 10 atmosphere pressure, and more preferably between about 1.2 and 5 atmosphere pressure. Generally, the time required for completion of the reaction is between 8 hours and 48 hours.

While not being bound by any particular theory, it is believed that high concentrations of reactants shifts the equilibrium of the condensation reaction to favor polyoxyalkylene ether products. While water is produced in the condensation reaction, the water concentration does not substantially affect the condensation reaction because the concentration of reactants is significantly higher than the concentration of water. In addition, the temperature and pressure parameters of the process of the present invention are believed to increase the rate at which the reactants react. Thus, the combination of high reactant concentration, temperature, and pressure parameters results in a process for the production of polyoxyalkylene ethers that does not require concomitant removal of water by-product during the condensation reaction.

The polyoxyalkylene ethers produced by the method of the invention range in purity from about 58% to about 90%. The method of the invention may be repeated to further enrich and purify the polyoxyalkylene ethers. In addition, after the reaction is complete, additional steps, such as an optional stripping step, may be performed to further purify the polyoxyalkylene ethers. Such an optional stripping step is suitably performed to remove volatile organic compounds from the product mixture. This step generally requires heating the product mixture under vacuum after the reaction is complete to an temperature sufficient to vaporize remaining aldehyde and/or volatile organic compounds, for example to approximately 60°–80° C. and 1 mm mercury (Hg) pressure for approximately 1 hour.

The polyoxyalkylene ethers made by the process of the present invention are useful as detergents, emulsifiers, wetting agents, penetrants, dye assistants, and the like, either alone or in combination with other ingredients.

The present invention is further described in detail by means of the following Examples. All parts and percentages are by weight unless explicitly stated otherwise, and all temperatures are in degrees Celsius.

EXAMPLES

EXAMPLE 1

20 g of a reaction product prepared from 1 mole of $C_9$ alkanol and 1 mole of propylene oxide, and 10 moles of ethylene oxide, 31.2 g of a reaction product prepared from 1 mole of $C_9$ alkanol and 1 mole of propylene oxide, and 15 moles of ethylene oxide, 0.98 g of a 95% paraformaldehyde, and 150 mg of concentrated sulfuric acid were charged to a 75 ml pressure reactor. The pressure reactor was sealed and placed in a 100° C. oven. After heating at about 100° C. for about 24 hours, the pressure reactor was removed and allowed to cool to room temperature. The reaction mixture was filtered and stripped at about 60°–80° C. and about 1 mm Hg for 1 hour to give a light yellow oil. $^{13}$C NMR analysis of the product showed that the product mixture exhibited 58% of the desired ether. This 58% pure ether was recharged to the pressure reactor and an additional 1.41 g of paraformaldehyde was added. The reactor was sealed and heated at 100° C. for another 24 hours. After removed from heating, the reactor was cooled to room temperature and opened. The reaction product was filtered, and stripped again to give a light yellow oil. $^{13}$C NMR analysis of the product exhibited a desired ether at 88% purity.

EXAMPLE 2

7 g of a reaction product prepared from 1 mole of $C_9$ alkanol, 1 mole of propylene oxide, and 15 moles of ethylene oxide, 0.33 g of paraformaldehyde, and 28 mg of a concentrated sulfuric acid were charged to a pressure reactor, sealed, and heated at 100° C. for about 24 hours. The reactor was then cooled to room temperature and opened.

The reaction product was filtered, and stripped at about 60°–80° C. and about 1 mm Hg for 1 hour to give a light yellow oil. $^{13}C$ NMR analysis of the product exhibited a desired ether at about 90% purity.

EXAMPLE 3

74.9 g of a reaction product prepared from 1 mole of $C_{13}$ alkanol, 1 mole of propylene oxide, and 12 moles of ethylene oxide, 4.56 g of paraformaldehyde, and 0.23 g of a concentrated sulfuric acid were charged to a pressure reactor, sealed, and heated at 100° C. for about 24 hours. The reactor was then cooled to room temperature, opened, and neutralized with 0.15 g of a 50% NaOH. After filtration and stripping as described above, a clear colorless oil was obtained. $^{13}C$ NMR analysis of the product exhibited a desired ether at about 78% purity.

EXAMPLE 4

50 g of a reaction product prepared from 1 mole of $C_{13}$ alkanol, 1 mole of propylene oxide, and 9 moles of ethylene oxide, 3.63 g of paraformaldehyde, and 0.15 g of a concentrated sulfuric acid were charged to a pressure reactor, sealed, and heated at 100° C. for about 24 hours. The reactor was then cooled to room temperature, opened, and neutralized with 0.15 g of a 50% NaOH. After filtration and stripping as described above, a clear colorless oil was obtained. $^{13}C$ NMR analysis of the product exhibited an ether at about 79% purity.

EXAMPLE 5

50 g of a reaction product prepared from 1 mole of $C_{13}$ alkanol, 1 mole of propylene oxide, and 6 moles of ethylene oxide, 4.4 g of paraformaldehyde, and 0.16 g of a concentrated sulfuric acid were charged to a pressure reactor, sealed, and heated at 100° C. for about 24 hours. The reactor was then cooled to room temperature, opened, and neutralized with 0.16 g of a 50% NaOH. After filtration and stripping as described above, a hazy colorless oil was obtained. $^{13}C$ NMR analysis of the product exhibited a desired ether at about 78% purity.

EXAMPLE 6

30 g of a reaction product prepared from 1 mole of $C_6$ alkanol, 1 mole of propylene oxide, and 9 moles of ethylene oxide, 3.41 g of a paraformaldehyde, and 0.1 g of a concentrated sulfuric acid were charged to a pressure reactor, sealed, and heated at 100° C. for about 24 hours. The reactor was then cooled to room temperature, opened, and neutralized with 0.1 g of a 50% NaOH. After filtration and stripping as described above, a hazy colorless oil was obtained. $^{13}C$ NMR analysis of the product exhibited a desired ether at about 82% purity.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for the preparation of polyoxyalkylene ether surfactant compositions having the formula

comprising the steps of:

providing an admixture of alkoxylated alcohols selected from the group consisting of

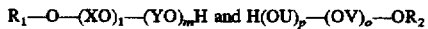

wherein $R_1$ and $R_2$ are independently selected from the group consisting of an alkyl or alkenyl groups having from 3 to 22 carbon atoms and a mono, di or trialkyl phenyl radical having from 14 to 26 carbon atoms;

$l$, $m$, $p$, $o$ are each integers from 0 to 30, and $l+m$ and $o+p$ are at least 3; and $X$, $Y$, $U$, $V$ are alkyl radicals;

combining said admixture of alkoxylated alcohols with an acid catalyst and aldehyde of the formula $R_3$—C(O)H wherein $R_3$ is H, an alkyl group, an alkenyl group, or an aryl group, said aldehyde being present in about 1–6 molar equivalents over the total moles of said alkoxylated alcohols; and reacting said combination at between about 500° and about 180° C. and at between about 1.2 atm and 10 atm pressure in the absence of a distillation step that removes water from the reaction, to produce said polyoxyalkylene ether surfactant composition.

2. The process of claim 1, wherein $R_1$ and $R_2$ are independently selected from the group consisting of an alkyl or alkenyl groups having from 6 to 18 carbon atoms and a mono, di or trialkyl phenyl radical having from 16 to 24 carbon atoms.

3. The process of claim 1, wherein $(XO)_1$, $(YO)_m$, $(OU)_o$ and $(OV)_p$ are alkoxy units independently selected from the group consisting of ethoxy, propoxy, isopropoxy, butoxy, and pentoxy.

4. The process of claim 1, wherein said aldehyde is selected from the group consisting of formaldehyde, acetaldehyde, propionaldehyde, butyraldehyde, benzaldehyde, and combinations thereof.

5. The process of claim 1, wherein said aldehyde is derived from a compound which releases said aldehyde during said reaction step.

6. The process of claim 5, wherein said compound is selected from the group consisting of trioxane, paraformaldehyde, and combinations thereof.

7. The process of claim 1, wherein said aldehyde is present from 1.5 to 3 molar equivalents over the total moles of said alkoxylated alcohols.

8. The process of claim 1, wherein said acid catalyst is selected from the group consisting of sulfuric acid, hydrochloric acid, phosphoric acid, organic sulfonic acid, Lewis acids, strongly acidic ion-exchange resins, and natural acid clays consisting of aluminum magnesium hydrosilicates.

9. The process of claim 1, wherein said reaction temperature is from about 80° C. to about 150° C.

10. The process of claim 1, wherein said reaction pressure is from about 1.2 atm and about 5 atm.

11. The process of claim 1, wherein said reacting step takes place for from about 8 hours to about 48 hours.

12. The process of claim 1, further comprising the step of repeating said combining step and said reacting step.

* * * * *

UNITED STATES PATENT AND TRADEMARK OFFICE
CERTIFICATE OF CORRECTION

PATENT NO. : 5,777,178 Page 1 of 1
APPLICATION NO. : 08/769619
DATED : July 7, 1998
INVENTOR(S) : Ming Shen It is certified that error appears in the above-identified patent and that said Letters Patent is hereby corrected as shown below:

In claim 1, column 6, at line 25, the temperature limitation of "500°" is incorrect.

The correct temperature limitation is --50° C.-- .

Signed and Sealed this

Nineteenth Day of December, 2006

JON W. DUDAS
*Director of the United States Patent and Trademark Office*